(12) United States Patent
Bäck et al.

(10) Patent No.: US 8,057,457 B2
(45) Date of Patent: Nov. 15, 2011

(54) BELTED ABSORBENT GARMENT

(75) Inventors: Lucas Bäck, Billdal (SE); Elisabeth Lakso, Stenungsund (SE); Stefan Nedestam, Mölnlycke (SE); Ingela Flink-Ekwall, Västra Frölunda (SE); Kent Hermansson, Västra Frölunda (SE); Gunnel Elglund, Kållered (SE)

(73) Assignee: SCA Hygience Products AB, Göteborg (SE)

( * ) Notice: Subject to any disclaimer, the term of this patent is extended or adjusted under 35 U.S.C. 154(b) by 209 days.

(21) Appl. No.: 12/305,685

(22) PCT Filed: Jun. 21, 2006

(86) PCT No.: PCT/SE2006/000752
§ 371 (c)(1),
(2), (4) Date: Dec. 19, 2008

(87) PCT Pub. No.: WO2007/149016
PCT Pub. Date: Dec. 27, 2007

(65) Prior Publication Data
US 2010/0217218 A1 Aug. 26, 2010

(51) Int. Cl.
*A61F 13/15* (2006.01)
*A61F 13/20* (2006.01)
(52) U.S. Cl. .................. 604/385.3; 604/392
(58) Field of Classification Search ........... 604/385.01, 604/385.21, 385.22, 385.23, 385.24, 385.25, 604/385.29, 385.3, 392; 2/75, 80, 111
See application file for complete search history.

(56) References Cited

U.S. PATENT DOCUMENTS

| | | | | |
|---|---|---|---|---|
| 2,638,899 A | * | 5/1953 | Ambarian | 604/397 |
| 2,739,595 A | * | 3/1956 | Huggins | 604/327 |
| 4,205,679 A | | 6/1980 | Repke et al. | |
| 4,627,853 A | | 12/1986 | Campbell et al. | |
| 4,916,005 A | | 4/1990 | Lippert et al. | |
| 4,938,817 A | | 7/1990 | Langley | |
| 4,964,860 A | | 10/1990 | Gipson et al. | |

(Continued)

FOREIGN PATENT DOCUMENTS

EP 0 287 338 A2 10/1988

(Continued)

OTHER PUBLICATIONS

U.S. Appl. No. 12/305,701, Kent Hermansson, "Belted Absorbent Garment", filed Dec. 19, 2008.

(Continued)

*Primary Examiner* — Alissa L Hoey
*Assistant Examiner* — Amber Anderson
(74) *Attorney, Agent, or Firm* — Buchanan Ingersoll & Rooney PC (57) ABSTRACT

Absorbent garment such as a diaper and an incontinence guard, said garment has a first body panel, a second body panel and a crotch portion there between. The garment is provided with opposed laterally extending belt members attached to the waist portion of the first body panel and are adapted to be wrapped around the waist of the wearer of the garment and fastened together by a first fastener. The second body panel at its waist portion is provided with second fasteners adapted to be fastened to the belt members, in such a way that the garment will assume a pant-like shape. An elastic member extends in transverse direction along the waist portion of the first body panel and extends into at least a portion of each belt member.

14 Claims, 4 Drawing Sheets

U.S. PATENT DOCUMENTS

| | | | |
|---|---|---|---|
| 4,988,346 A * | 1/1991 | Pfefferkorn | 604/389 |
| 5,135,522 A * | 8/1992 | Fahrenkrug et al. | 604/385.3 |
| 5,209,743 A * | 5/1993 | Hardison | 604/391 |
| 5,226,992 A | 7/1993 | Morman | |
| 5,261,901 A * | 11/1993 | Guay | 604/391 |
| 5,295,986 A * | 3/1994 | Zehner et al. | 604/385.25 |
| 5,304,162 A * | 4/1994 | Kuen | 604/391 |
| 5,368,585 A * | 11/1994 | Dokken | 604/393 |
| 5,370,634 A * | 12/1994 | Ando et al. | 604/385.21 |
| H001440 H * | 5/1995 | New et al. | 604/386 |
| 5,626,574 A | 5/1997 | Sasaki et al. | |
| H001674 H * | 8/1997 | Ames et al. | 604/389 |
| 5,919,539 A | 7/1999 | Bisbis et al. | |
| 6,086,571 A | 7/2000 | Guevara et al. | |
| 6,245,051 B1 | 6/2001 | Zenker et al. | |
| D456,508 S * | 4/2002 | Schroeder et al. | D24/126 |
| D457,950 S * | 5/2002 | Schroeder et al. | D24/126 |
| 6,572,601 B2 * | 6/2003 | Suprise et al. | 604/391 |
| 6,616,648 B2 * | 9/2003 | Hermansson et al. | 604/385.27 |
| 6,713,159 B1 | 3/2004 | Blenke et al. | |
| 6,764,479 B2 * | 7/2004 | Kusibojoska et al. | 604/385.3 |
| 2001/0041879 A1 * | 11/2001 | Karami et al. | 604/386 |
| 2004/0116889 A1 | 6/2004 | Carbone, II et al. | |
| 2005/0131373 A1 | 6/2005 | Wright et al. | |

FOREIGN PATENT DOCUMENTS

| | | |
|---|---|---|
| EP | 0 409 307 A2 | 1/1991 |
| EP | 0 487 758 A1 | 6/1992 |
| EP | 0 605 012 A1 | 7/1994 |
| EP | 0 646 062 | 4/1995 |
| EP | 1 035 818 | 9/2000 |
| EP | 1 077 054 A2 | 2/2001 |
| EP | 1 110 529 A1 | 6/2001 |
| EP | 1 236 456 A2 | 9/2002 |
| FR | 2 582 517 A1 | 12/1986 |
| FR | 2 586 558 A1 | 3/1987 |
| GB | 1 332 037 | 10/1973 |
| JP | 3471999 | 6/1997 |
| WO | WO 91/08725 A1 | 6/1991 |
| WO | WO 94/00292 A1 | 1/1994 |
| WO | WO 98/29251 A1 | 7/1998 |
| WO | WO 99/27876 A1 | 6/1999 |
| WO | WO 01/00129 A1 | 1/2001 |
| WO | WO 02/32364 A1 | 4/2002 |
| WO | WO 03/000165 | 1/2003 |
| WO | WO 03/047488 A1 | 6/2003 |
| WO | WO 2004/017885 A2 | 3/2004 |

OTHER PUBLICATIONS

U.S. Appl. No. 12/307,964, Lucas Back, "Seam Joining Together at Least Two Web Materials", filed Jan. 8, 2009.

Form PCT/ISA/210 (International Search Report) dated Feb. 2, 2007.

Form PCT/ISA/237 (Written Opinion of the International Searching Authority) dated Feb. 2, 2007.

* cited by examiner

Fig. 6

BELTED ABSORBENT GARMENT

TECHNICAL FIELD

The present disclosure refers to an absorbent garment such as a diaper and an incontinence guard provided with a belt as part of the fastening means for attaching the garment around the waist of the wearer.

BACKGROUND

So called belted absorbent garments comprise a front body panel adapted to be applied over the stomach of the wearer, a back body panel adapted to be applied over the back of the wearer and a crotch portion adapted to extend over the crotch of the wearer between the legs. The garment further comprises a pair of opposed laterally extending belt members usually attached to the back panel at the waist portion thereof. These belt portions are adapted to be wrapped around the waist of the wearer of the garment and fastened together by a first fastener, such as an adhesive tape or mechanical fasteners, for example a hook-and-loop fastener. The front panel is then passed between the legs of the wearer and fastened to the outside or inside of the belt members by second fasteners provided at the waist portion of the front panel. The garment will then assume a pant-like shape. Alternatively the belt portions are arranged at the front panel and the second fasteners at the back panel. Since often the front and back panels are more or less identical as to shape and size the wearer or caretaker may apply the article after individual preference, so that the front panel may be used as back panel and vice versa.

The belt provides for improved possibilities to adjust the fit of the absorbent garment. It further simplifies the change of the garment especially when the wearer is standing up.

Examples of belted absorbent garments are found in for example EP-A-0 287 388, EP-A-0 409 307, EP-A-0 605 012 and FR-A-2 586 558.

It is also known to make part of the belt elastic in order to further improve comfort and fit. JP-B-3471999 discloses a belted diaper wherein the belt portions have a stretchable part at the respective base end thereof, which allows the belt portions to be extended along their length direction. The back panel of the diaper is further provided with an elastic portion (waist elastics).

EP-B-0 487 758 also discloses a belted diaper in which at least one belt member has an elastic portion. The back panel of the diaper is also provided with elastic members.

The incorporation of several separate elastic members in an absorbent garment is however complicated in a manufacturing process and makes the garment more expensive.

SUMMARY

The present disclosure aims at providing a belted absorbent garment having improved comfort and fit and which can be made with a cost-efficient manufacturing process. This has been accomplished by a garment of the above mentioned kind having an elastic member which extends in transverse direction along the waist portion of the first body panel and extends laterally beyond said first body panel into at least a portion of each belt member. Making a belted absorbent garment comprising a single continuous elastic member that is long enough to extend in transverse direction along the waist portion of the first body panel and along at least a part of each belt member is less complicated than to manufacture an garment having a partially elastic belt and a separate waist elastics in the first body panel to which the belt portions are attached.

The garment further provides an improved fit and a good sealing effect in the waist area.

In one embodiment the elastic member extends over no more than 50% of the length of each belt member, preferably over no more than 40% and more preferably over no more than 30% of the length of each belt member.

In a further aspect the elastic member extends over a length of at least 1 cm, preferably at least 2 cm, of each laterally extending belt member.

The elastic member may comprise an elastic film or an elastic laminate. Alternatively it comprises one or more elastic threads or strips.

In one embodiment the elastic member extends over and is attached in a face-to-face relationship to the waist portion of the first body panel either to the garment facing side thereof or to the wearer facing side thereof or between material layers contained in the first body panel.

In an alternative embodiment the elastic member is attached to a distal edge of the waist portion of the first body panel so as to form a separate waist band.

According to one aspect of the disclosure an elastic member extends in transverse direction along at least part of the waist portion of the second body panel.

The first and second fasteners according to one embodiment comprise hook members and at least part of the external surface of the belt members facing away from the wearer's body is of a material adapted to act as a loop material engaging with said hook members.

In one embodiment of the disclosure the portion of the elastic member extending into the respective belt member is provided with a contrasting colour, pattern or marking so as to be distinguishable from the rest of the belt member, or alternatively that said rest of the belt member is provided with a contrasting colour, pattern or marking so as to be distinguishable from said portion of the elastic member.

BRIEF DESCRIPTION OF THE DRAWINGS

The disclosure will in the following be closer described with reference to non-limiting embodiments shown in the accompanying drawings.

DESCRIPTION OF PREFERRED EMBODIMENTS

Figure 1:
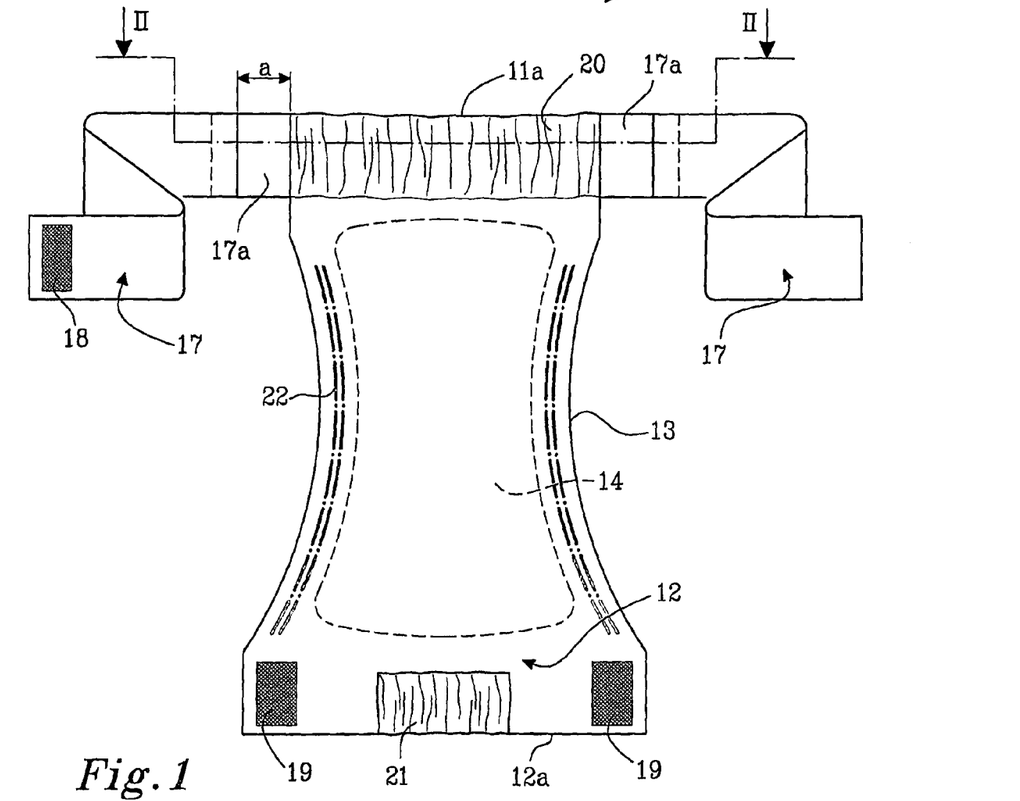
FIG. 1 shows a plan view of a belted diaper according to one embodiment of the disclosure.

FIG. 1 of the drawings shows an embodiment of an absorbent garment in the form of a diaper or incontinence guard 10 comprising a first body panel 11, which in the embodiment shown in the drawings is the part of the garment that in use is intended to extend over the back and the rear hip area of the wearer. The garment also comprises a second body panel 12, which in the shown embodiment is the part of the pant diaper that in use is intended to extend over the stomach and front hip area of the wearer. Each of said first and second body panels 11 and 12 has a waist portion 11a and 12a respectively. It is understood that alternatively the first body panel 11 may be the front body panel and the second body panel 12 may be the back body panel. The crotch portion 13 of a garment 10 is the part of the garment that in use is intended to extend through the wearer's crotch area, between the legs. An absorbent core 14 is disposed in the crotch portion 13 and extends into the front and back body panels 11 and 12. The absorbent core 14 is disposed between an inner coversheet 15 and an outer coversheet 16. The garment has a longitudinal direction x and a transverse direction y.

The term "inner coversheet" refers to the liquid permeable material sheet forming the inner cover of the absorbent garment and which in use is placed in direct contact with the skin of the wearer. The inner coversheet can comprise a nonwoven material, e.g. spunbond, meltblown, carded, hydroentangled, wetlaid etc. Suitable nonwoven materials can be composed of natural fibers, such as wood pulp or cotton fibres, man-made fibres, such as polyester, polyethylene, polypropylene, viscose, rayon etc. or from a mixture of natural and man-made fibres. The inner coversheet material may further be composed of tow fibres, which may be bonded to each other in a bonding pattern, as e.g. disclosed in EP-A-1 035 818. Further examples of inner coversheet materials are porous foams, apertured plastic films etc. The materials suited as inner coversheet materials should be soft and non-irritating to the skin and be readily penetrated by body fluid, e.g. urine or menstrual fluid. The inner coversheet may further be different in different parts of the absorbent garment.

The "outer coversheet" refers to the material forming the outer cover of the absorbent garment. The outer coversheet may be the same or different in different parts of the absorbent garment. At least in the area of the absorbent core the outer coversheet comprises a liquid impervious material a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The outer coversheet material may be breathable so as to allow vapour to escape from the absorbent core, while still preventing liquids from passing therethrough. Examples of breathable outer coversheet materials are porous polymeric films, nonwoven laminates of spunbond and meltblown layers and laminates of porous polymeric films and nonwoven materials. Preferably, the outer coversheet comprises a nonwoven material on at least the undergarment-facing surface thereof.

The "absorbent core" is the absorbent structure disposed between the two coversheets of the absorbent garment in at least the crotch region thereof. The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent composites including particles, fibres, flakes, spheres, and the like.

A high liquid storage capacity is provided by the use of high amounts of superabsorbent material. For an absorbent core comprising a matrix of hydrophilic fibres, such as cellulosic fibres, and superabsorbent material, the proportion of superabsorbent material is preferably between 10 and 90% by weight, more preferably between 30 and 70% by weight.

It is conventional for absorbent garments to have absorbent cores comprising layers of different properties with respect to liquid receiving capacity, liquid distribution capacity and storage capacity. The thin absorbent bodies, which are common in for example baby diapers and incontinence guards, often comprise a compressed, mixed or layered structure of cellulosic fluff pulp and superabsorbent polymers. The size and absorbent capacity of the absorbent core may be varied to suit different uses, such as infants or adult incontinent persons.

The absorbent core may further include an acquisition distribution layer placed on top of the primary absorbent body, which is adapted to quickly receive and temporarily store discharged liquid before it is absorbed by the primaryy absorbent core. Such acquisition distribution layers are well known in the art and may be composed of porous fibrous wadding or foam materials.

Figure 5:
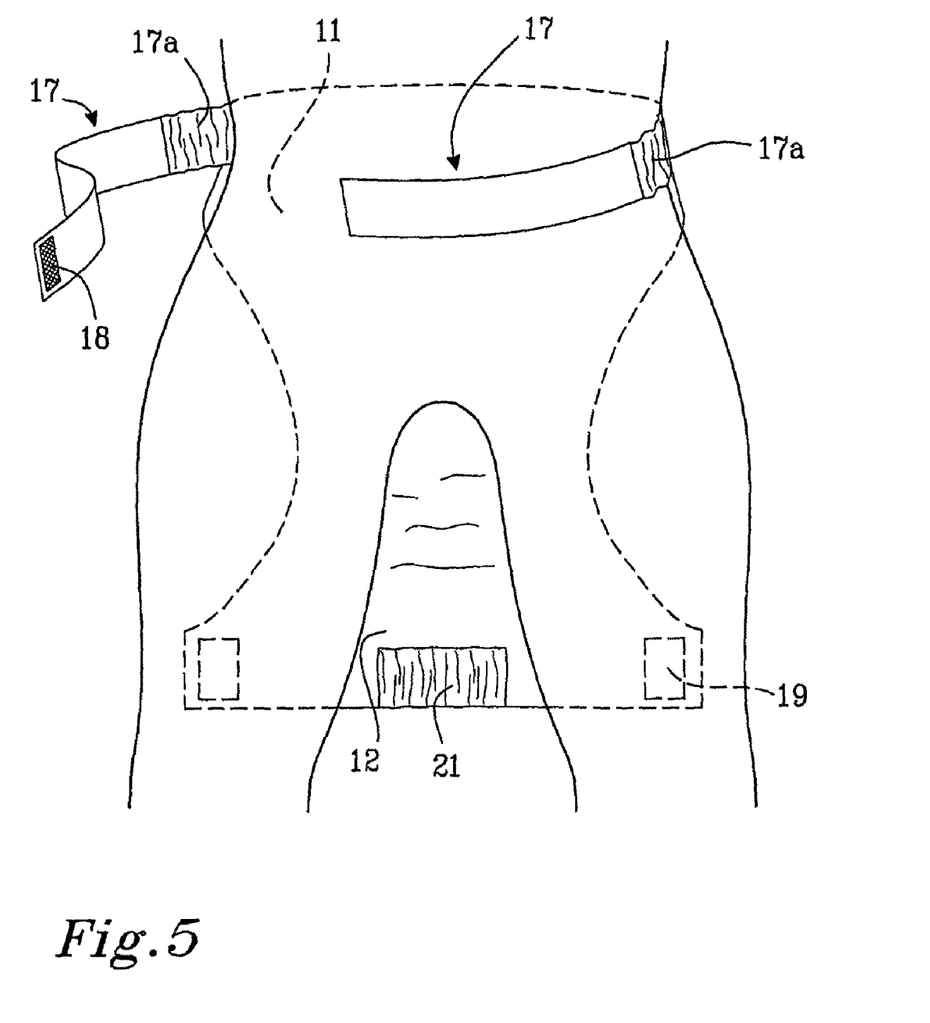
FIGS. 5 and 6 illustrate how a belted diaper is put on a wearer.

A pair of belt members 17 are attached to the waist portion of first body panel 11 and are intended to be wrapped around the waist of the wearer of the garment and fastened together by first fastener 18, for example a mechanical fastener, especially a hook fastener of a hook-and-loop fastener. This is illustrated in FIG. 5.

The external surface of the opposite belt member, especially if this comprises a fibrous nonwoven, may function as a loop member. Further examples of mechanical fasteners are button and holes or button loops, snap fasteners and the like. The buttons can either be fastened to the belt or to the garment.

A "hook-and-loop fastener" refers to complementary fastener portions having a "hook" portion and a "loop" portion and which are refastenable. The term "hook" as used herein refers to any element capable of engaging another element, the so called "loop" portion. The term "hook" is not limited to only "hooks" in its normal sense, but rather encompasses any form of engaging elements, whether unidirectional or bi-directional. The term "loop" is likewise not limited to "loops" in its normal sense, but also encompasses any structure capable of engaging with a "hook" fastener. Examples of "loop" materials are fibrous structures, like nonwoven materials. Hook-and-loop fasteners are for example available from Velcro, USA.

Alternatively the first fastener 18 is an adhesive fastener such as a tape tab, wherein the external surface of opposite belt member 17 may be of a material to which the tape can adhere.

The width of the belt members 17 should be from 5 to 20 cm, preferably from 7 to 15 cm.

The belt members 17 are for example made from a laminate of a carrier material, which forms the external surface of the belt, and a soft nonwoven, which forms the inside of the belt which is intended to be in direct contact with the skin of the user.

A suitable nonwoven material can be a spunbond material of e.g. polypropylene or polyethylene fibres. Conjugate fibres may also be used. Another suitable nonwoven material is formed from a carded thermobonded material of e.g. polypropylene, polyester or conjugate fibres.

The external surface of the belt members, for example the carrier material, should be adapted to function as a reception surface for the fastener 18. In case the fastener is a hook fastener a nonwoven material may be used as a carrier material. In case the fastener 18 is a tape tab, a plastic film is suitable as carrier material.

Figure 6:
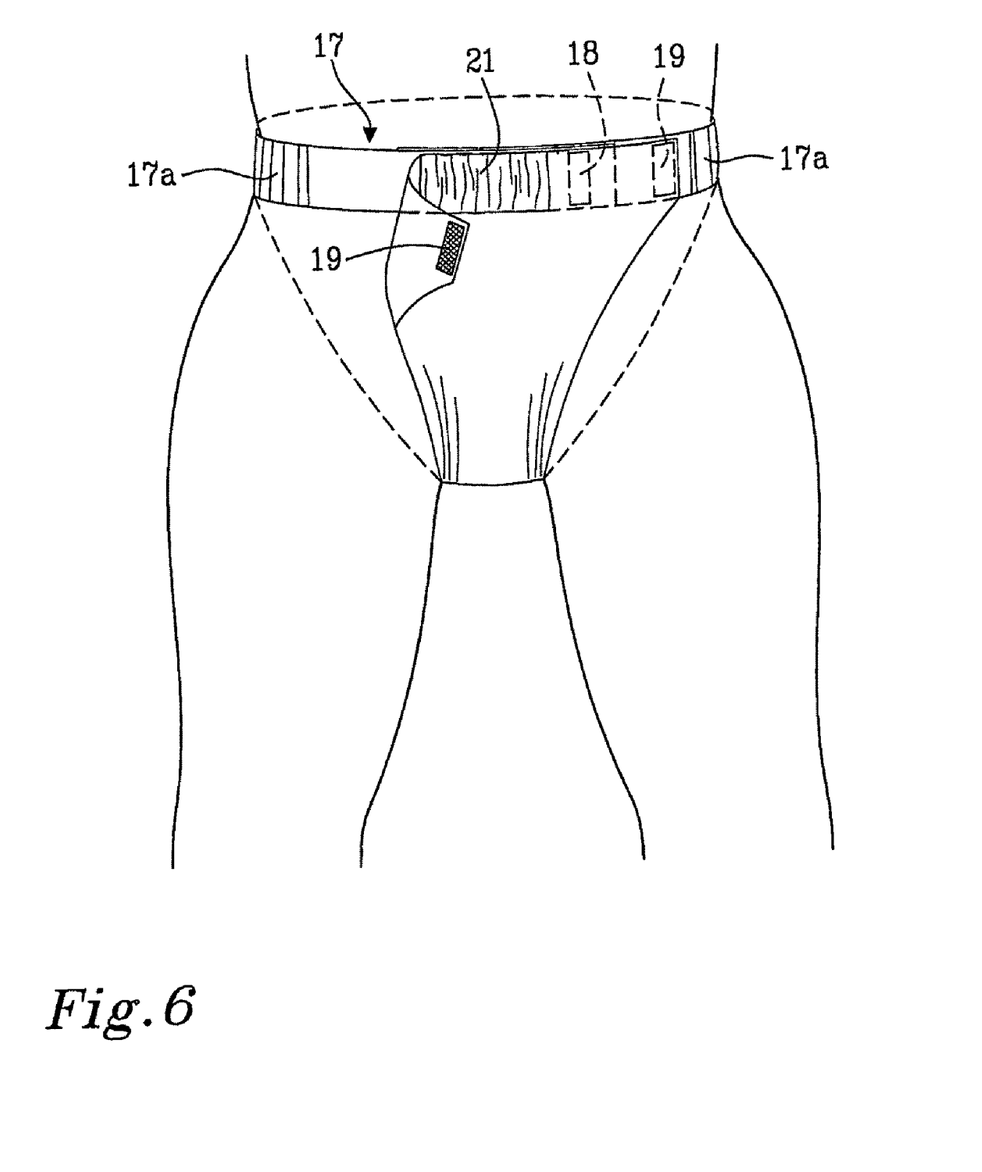

The front panel 12 is then passed between the legs of the wearer and fastened to the outside of the belt members by second fasteners 19 provided at the lateral edges of the waist portion 12a of the front panel 12. This is illustrated in FIG. 6. These second fasteners 19 may be mechanical fasteners, such as hook fasteners, button and holes or button loops or adhesive tape fasteners.

A continuous elastic member 20 extends in transverse direction, x, along the waist portion 11a of the first body panel 11 and extends into at least a portion of each belt member 17. Said elastic member 20 may be in the form of an elastic web material such as an elastic film, an elastic nonwoven, an elastic laminate or the like. The elastic laminate may be a laminate between two or more nonwoven layers, two or more film layers or a combination of film and nonwoven layers.

Examples of elastic laminates suitable for forming said elastic member 20 are any elastic laminate known in the art. One group of elastic laminates are so called "stretch-bonded" laminates, in which the elastic layer is stretched in at least one direction before laminating it with one or more inelastic layers. After the tension is removed from the elastic layer it can freely retract to its untensioned state, and the inelastic layer(s) laminated thereto become gathered, giving a three-dimensional puckering.

Another group of elastic laminates are so called "neck bonded" laminates, which refer laminates in which an elastic material is bonded to a non-elastic material while the non-elastic member is extended under conditions reducing its width or necked. "Neck bonded laminate" refers to a composite material having at least two layers in which one layer is a necked, non-elastic layer and the other layer is an elastic layer. The layers are joined together when the non-elastic layer is in an extended condition.

A further group of elastic laminates are disclosed in for example WO/047488, in which inelastic nonwoven layers are laminated to an elastic film layer, and the laminate is stretched above the point of failure of the nonwoven materials, so that the inelastic layers break.

Examples of elastic laminates are described in EP-B-0 646 062, WO 98/29251, WO 03/000165 and U.S. Pat. No. 5,226, 992. Examples of commercially available elastic laminates are Fabriflex 306 from Tredegar and PK 6358 from Nordenia.

In an alternative embodiment the continuous elastic member 20 comprises one or more elastic threads or strips contractably affixed between the outer coversheet 13 and the inner coversheet 12.

The elastic member 20 should have an elasticity of at least 30% as measured in the elasticity test as described below.

Figure 2:
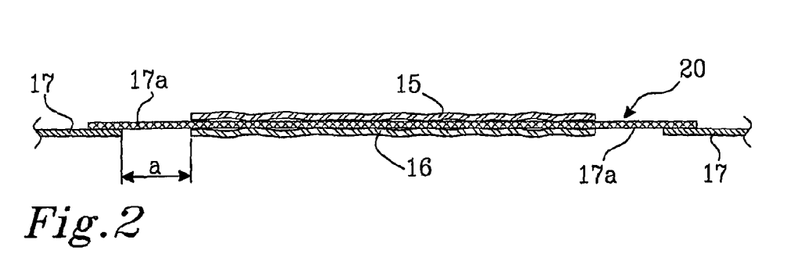
FIG. 2 is a section according to the line II-II in FIG. 1.

In the embodiment shown in FIGS. 1 and 2 the elastic member 20 is in the form of an elastic web material extending along the waist portion of the first body panel 11 between the inner and outer coversheets 15 and 16 and laterally outside thereof so as to form elastic proximal end regions 17a of each belt member 17. The elastic member 20 is attached by gluing, ultrasonic welding, thermobonding or other suitable bonding technique to the proximal portion of the respective belt member 17, which preferably is inelastic or at least less elastic than the elastic member 20. Since the part of the elastic that extends along the waist portion of the first body panel 11 is applied between two material layers, the inner and outer coversheets, the elastic member may in one alternative embodiment be only partially laminated, so that the part applied between the inner and outer coversheets may for example only comprise an elastic film layer, while those portions of the elastic member 20 that extend laterally outside of the first body panel 11 are laminated to nonwoven layers, for example.

In alternative embodiments the elastic web material 20 is attached to the garment facing side of the outer coversheet 16 or to the wearer facing side of the inner coversheet 15.

It is preferred that the elastic member 20 does not extend over more than 50% of the length of each belt member, preferably over no more than 40% and more preferably over no more than 30% of the length of each belt member 17. This since the effectiveness of the fasteners 18 and 19 is decreased if attached to an elastic region, since the elastic region may expand and/or contract and thereby weaken the bond between the fasteners and the elastic region. It is further preferred that the active part of the elastic member 20 extends over a length, a, of at least 1 cm, preferably at least 2 cm, of each laterally extending belt member 17. The active part, a, of the elastic member 20 refers to the part of the elastic member which has not been made inactive due to bonding to the in-elastic belt members 17. This is shown in FIG. 2. Thus the part of the elastic member 20 overlapping with and bonded to the inelastic belt members 17 are not included in the active part, a.

The elastic member 20 provides for an improved comfort and fit around the waist of the wearer. In addition it simplifies the manufacturing process and makes it more cost-efficient, since the waist elastics and the elastic attachment of the belt members 17 to the first body panel 11 are made in one single step A waist elastic member 21 extends in transverse direction, x, along at least part of the waist portion 12a of the second body panel 12. The waist elastic member may be an elastic web material such as an elastic laminate, an elastic film, an elastic nonwoven or the like contractably attached between the inner and outer coversheets, to the external side of the outer coversheet or to the wearer facing side of the inner coversheet. Alternatively it comprises two or more elastic threads or strips contractably affixed between the outer and inner coversheets.

The leg openings may be elasticized, said elastification is usually accomplished by a plurality of elastic members 22, such as elastic threads, which are contractably affixed between the outer and inner coversheets. The garment may also be provided by so called barrier cuffs, in order to provide an improved security against leakage. These barrier cuffs may in some instance replace leg elastics.

Figure 3:
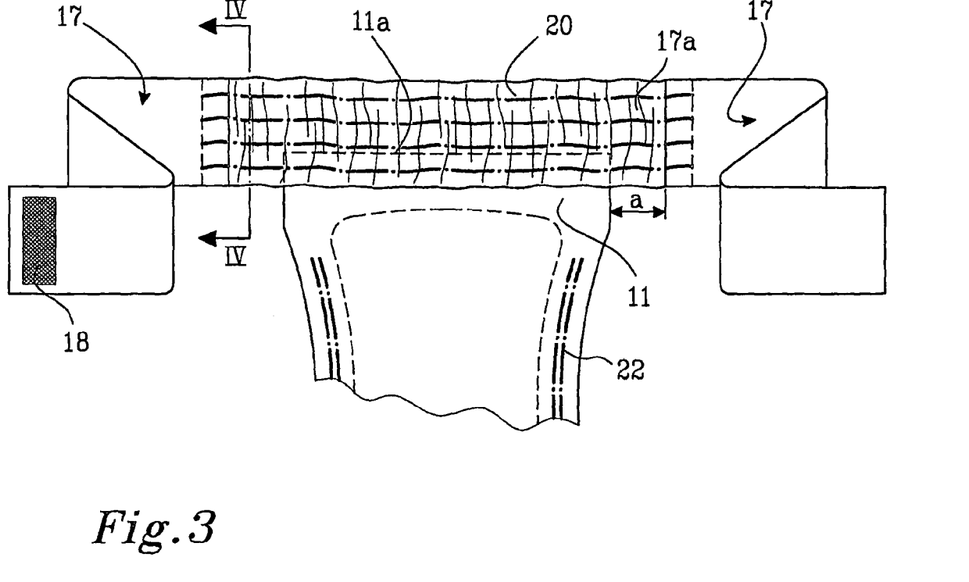
FIG. 3 is a plan view of an alternative embodiment of a belted diaper according to the disclosure.
Figure 4:
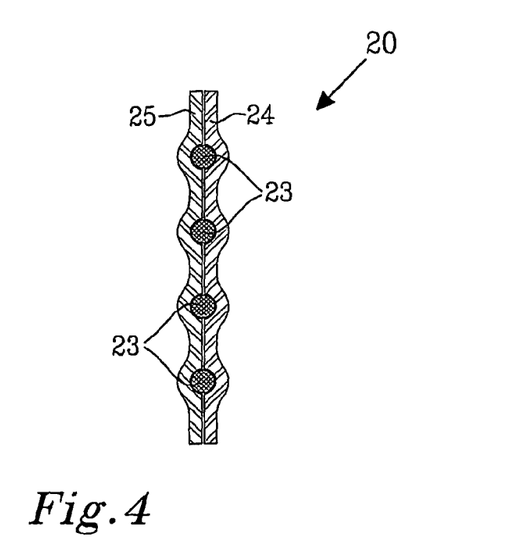
FIG. 4 is a section according to the line IV-IV in FIG. 3.

In the embodiment shown in FIGS. 3 and 4 the continuous elastic member 20 is attached to a distal edge of the waist portion 11a of the first body panel 11 so as to form a separate waist band of the garment. The elastic member/waist band 20 extends laterally outside the first body panel a distance, a, of at least 1 cm, preferably at least 2 cm, at its respective lateral side edges, so as to form elastic proximal end regions 17a of each belt member 17. It is preferred that the elastic member 20 does not extend over more than 50% of the length of each belt member, preferably over no more than 40% and more preferably over no more than 30% of the length of each belt member 17.

The continuous elastic member 20 shown in FIGS. 3 and 4 comprises a plurality of elastic threads 23 contractably affixed between web material layers 24, 25. In an alternative embodiment it comprises an elastic web material such as an elastic film, an elastic nonwoven, an elastic laminate or the like as discussed above.

In one embodiment of the disclosure the elastic regions 17a of the belt members are indicated by a contrasting colour, pattern or marking, so as to be readily distinguishable to the user or caregiver for indicating that this region should not be used as an attachment surface for the fasteners 18, 19, for the reasons given above. Alternatively the non-elastic portions of the belt members 17 are indicated with said contrasting colour, pattern or marking for indicating that this region should be used as attachment surface.

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample is centred and fastened perpendicularly in the clamps. The tensile tester is started and three cycles between 0 and the predetermined elongation, equal to the highest defined $1^{st}$ load, are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus an elasticity of 30% is defined as that the laminate should have a permanent relaxation after elongation of less than 10% after being exerted to an elongation of 30% in the tensile tester above. An elongation of 30% means an elongation to a length that is 30% longer than the initial length of the sample.

Although only a few exemplary embodiments have been described in detail above, those skilled in the art will readily understand that many modification are possible and that any such modifications are intended to be included within the scope of this invention. Accordingly, it is to be understood that the invention should not be considered as limited by the above description; rather the scope and limitations of the inventions are defined solely by the granted claims, and equivalents thereof.

The invention claimed is:

1. An absorbent garment, said garment having a longitudinal and a transverse direction and comprises a first body panel, a second body panel and a crotch portion there between, each of said first and second body panels having a waist portion, said garment further being provided with opposed laterally extending first and second belt members attached to the waist portion of first body panel and being adapted to be wrapped around the waist of the wearer of the garment and fastened together by a first fastener, the second body panel at its waist portion being provided with second fasteners adapted to be fastened to the belt members, in such a way that the garment will assume a pant-like shape, wherein an elastic member extends continuously in transverse direction across the entire waist portion of the first body panel and extends laterally beyond said first body panel into each belt member and over no more than 50% of the length of each belt member, so as to form elastic proximal end regions of each belt member, the first belt member comprising the elastic member, a first inelastic member, and the first fastener, the first inelastic member having a proximal end and a distal end, the proximal end being closer to the first body panel than the distal end, wherein the elastic member overlaps the proximal end of the first inelastic member and wherein the first fastener is attached to the distal end of the first inelastic member, the second belt member comprising the elastic member and a second inelastic member, the second inelastic member having a proximal end and a distal end, the proximal end being closer to the first body panel than the distal end, wherein the elastic member overlaps the proximal end of the second inelastic member.

2. The absorbent garment according to claim 1, wherein said elastic member extends over no more than 40% of the length of each belt member.

3. The absorbent garment according to claim 2, wherein the elastic member, in the first belt member, includes a first active part that is not attached to the first inelastic member, wherein the first active part extends over a length of at least 1 cm of the first belt member, and wherein the elastic member, in the second belt member, includes a second active part that is not attached to the second inelastic member, wherein the second active part extends over a length of at least 1 cm of the second belt member.

4. The absorbent garment according to claim 1, wherein the elastic member comprises an elastic film, an elastic nonwoven or an elastic laminate.

5. The absorbent garment according to claim 1, wherein the elastic member comprises one or more elastic threads or strips.

6. The absorbent garment according to claim 1, wherein the elastic member extends over and is attached in a face-to-face relationship to the waist portion of the first body panel to the garment facing side thereof.

7. The absorbent garment according to claim 1, wherein the elastic member is attached to a distal edge of the waist portion of the first body panel so as to form a separate waist band.

8. The absorbent garment according to claim 1, wherein a second elastic member extends in transverse direction along at least part of the waist portion of the second body panel.

9. The absorbent garment according to claim 1, wherein the first and second fasteners comprise hook members and that at least part of the external surface of the belt members facing away from the wearer's body is of a material adapted to act as a loop material engaging with said hook members.

10. The absorbent garment according to claim 1, wherein the portion of the elastic member extending into the respective belt member is provided with a contrasting colour, pattern or marking so as to be distinguishable from the rest of the belt member, or that said rest of the belt member is provided with a contrasting colour, pattern or marking so as to be distinguishable from said portion of the elastic member.

11. The absorbent garment according to claim 1, wherein said elastic member extends over no more than 30% of the length of each belt member.

12. The absorbent garment according to claim 1, wherein the first body panel has two terminal side edges and a terminal distal edge, wherein the elastic member is attached to each terminal side edge and extends from each terminal side edge.

13. An absorbent garment, said garment having a longitudinal and a transverse direction and comprises a first body panel, a second body panel and a crotch portion there between, each of said first and second body panels having a waist portion, said garment further being provided with opposed laterally extending first and second belt members attached to the waist portion of first body panel and being adapted to be wrapped around the waist of the wearer of the garment and fastened together by a first fastener, the second body panel at its waist portion being provided with second fasteners adapted to be fastened to the belt members, in such a way that the garment will assume a pant-like shape, wherein an elastic member extends continuously in transverse direction across the entire waist portion of the first body panel and extends laterally beyond said first body panel into each belt member and over no more than 50% of the length of each belt member, so as to form elastic proximal end regions of each belt member, wherein the elastic member extends over and is attached in a face-to-face relationship to the waist portion of the first body panel to the wearer facing side thereof, the first belt member comprising the elastic member, a first inelastic member, and the first fastener, the first inelastic member having a proximal end and a distal end, the proximal end being closer to the first body panel than the distal end, wherein the elastic member overlaps the proximal end of the first inelastic member and wherein the first fastener is attached to the distal end of the first inelastic member, the second belt member comprising the elastic member and a second inelastic member, the second inelastic member having a proximal end and a distal end, the proximal end being closer to the first body panel than the distal end, wherein the elastic member overlaps the proximal end of the second inelastic member.

14. An absorbent garment, said garment having a longitudinal and a transverse direction and comprises a first body panel, a second body panel and a crotch portion there between, each of said first and second body panels having a waist portion, said garment further being provided with opposed laterally extending first and second belt members attached to the waist portion of first body panel and being adapted to be wrapped around the waist of the wearer of the garment and fastened together by a first fastener, the second body panel at its waist portion being provided with second fasteners adapted to be fastened to the belt members, in such a way that the garment will assume a pant-like shape, wherein an elastic member extends continuously in transverse direction across the entire waist portion of the first body panel and extends laterally beyond said first body panel into each belt member and over no more than 50% of the length of each belt member, so as to form elastic proximal end regions of each belt member, wherein the elastic member extends between material layers contained in the first body panel, the first belt member comprising the elastic member, a first inelastic member, and the first fastener, the first inelastic member having a proximal end and a distal end, the proximal end being closer to the first body panel than the distal end, wherein the elastic member overlaps the proximal end of the first inelastic member and wherein the first fastener is attached to the distal end of the first inelastic member, the second belt member comprising the elastic member and a second inelastic member, the second inelastic member having a proximal end and a distal end, the proximal end being closer to the first body panel than the distal end, wherein the elastic member overlaps the proximal end of the second inelastic member.

\* \* \* \* \*